United States Patent [19]

Williams

[11] 4,425,447

[45] Jan. 10, 1984

[54] FLAME RETARDANT POLYMER COMPOSITION

[75] Inventor: David O. Williams, Hoffman Estates, Ill.

[73] Assignee: Saytech, Inc., Sayreville, N.J.

[21] Appl. No.: 367,283

[22] Filed: Apr. 12, 1982

[51] Int. Cl.$^3$ .............................. C08J 9/00; B32B 5/20; C08G 18/14

[52] U.S. Cl. .................................. 521/132; 521/906; 521/907; 521/131; 524/469

[58] Field of Search ....................... 521/132, 906, 907; 524/469

[56] References Cited

U.S. PATENT DOCUMENTS 4,232,085  11/1980  Carlstrom et al. .................. 428/315

Primary Examiner—Morton Foelak
Attorney, Agent, or Firm—Donald L. Johnson; John F. Sieberth; Teresa M. Stanek

[57] ABSTRACT

A polymer composition containing a flame retardant amount of tribromocumene. The polymer is preferably polyurethane and may be either foamed or non-foamed.

2 Claims, No Drawings

FLAME RETARDANT POLYMER COMPOSITION

BACKGROUND OF THE INVENTION

1. Field of the Invention

This invention relates to a flame retardant, self-extinguishing polymer composition. More particularly, this invention relates to the use of tribromocumene as a flame retardant additive in polymers. A polymer of particular interest is polyurethane.

2. Description of the Prior Art

The problem of the flammability of polymers has received considerable attention. A variety of compounds exist that provide satisfactory flame resistance, smoke suppression and self-extinguishing properties.

The conventional flame retarding agents for polymers fall within two categories. They are either reactive or additive. The reactive compounds are incorporated into the structure or backbone of the polyurethane. Additive flame retardants are only physically incorporated into the polymerized product. Both reactive and additive flame retardant compounds may be present in the same system.

Polyurethanes are one type of polymer that are usually prepared by combining a liquid polyol, such as a polyester, glycol or polyglycol, with a stoichiometric equivalent of a liquid organic polyisocyanate in the presence of a suitable catalyst. Both solid and liquid flame retardant compounds have application in polyurethanes. One solid additive designed for use in flexible polyurethane foam is pentabromoethylbenzene described in U.S. Pat. No. 4,232,085. Other solid flame retardant compounds used in polyurethane compositions are tetrabromoethylcyclohexane and N,N'-1,2-ethane-bis(5,6-dibromonorbornane-2,3-dicarboximide). When trying to incorporate these solid additives into the liquid polyol/liquid polyisocyanate systems it is difficult to prevent the solid flame retardant from volatilizing. The use of a liquid flame retardant in these polyurethane compositions would be advantageous. It has been discovered that tribromocumene, a liquid flame retardant additive with low volatility, is an effective flame retardant in polymer compositions. Since tribromocumene is a liquid it is of special interest in polyurethanes.

SUMMARY OF THE INVENTION

According to the present invention, tribromocumene is an effective flame retardant additive in polymer compositions.

DESCRIPTION OF THE PREFERRED EMBODIMENTS

Polyurethanes have the characteristic structure

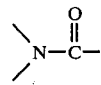

The term "polyurethane" as used in this invention does not actually contain primarily urethane groups, but are those polymers which contain significant numbers of urethane groups regardless of what the rest of the molecule may be. Compounds containing groups such as amino and carboxyl may also be used. Thus, a typical polyurethane may contain, in addition to urethane groups, aliphatic and aromatic hydrocarbon residues, ester, ether, amide and urea groups.

A preferred embodiment of the present invention is a polyurethane composition containing a flame retardant amount of tribromocumene. A more preferred embodiment is a flame retardant, self-extinguishing polyurethane comprising an organic polyol, sufficient organic polyisocyanate to combine with solid polyol to produce polyurethane, a catalyst and a sufficient amount of tribromocumene to impart flame retardant properties to the polyurethane.

Any suitable organic polyol or combination of polyols, including both aliphatic and aromatic may be used, such as polyether polyols and mixtures of polyether polyols and poly(ethylene glycol) adducts of pentaerythritol, sucrose, sorbitol, alphamethylglucoside, butanediol, trimethylolpropane, and the like.

The organic polyisocyanates used in the manufacture of polyurethanes are known to the art. Any organic polyisocyanate is suitably employed in producing the flame-retardant compositions of this invention. Combinations of polyisocyanates may also be used. Typical examples of suitable polyisocyanates for use in preparing the flame-retardant polyurethanes of this invention are:

1,6-hexamethylene diisocyanate,
1,4-tetramethylene diisocyanate,
m-phenylene diisocyanate,
1-methoxyphenyl-2,4-diisocyanate,
4,4',4''-triphenylmethane triisocyanate,
4,4'-dimethyldiphenylmethane-2,2',5,5'-tetraisocyanate,
toluene diisocyanate and
methylene-bis(phenylisocyanate).

The amount of polyisocyanate employed varies slightly depending upon the nature of the polyurethane being prepared. A sufficient amount of organic polyisocyanate is used to stoichiometrically combine with the organic polyol to produce polyurethane. In general, the polyisocyanates are employed in amounts that provide from 80 to 150 percent, preferably from 90 to 120 percent of the stoichiometric amount of the isocyanate groups required to react with the reactive hydrogen atoms present on the hydroxyl groups or amino groups of the reactants in the polyurethane-producing reaction mixture.

Any of the conventional catalysts employed in polyurethane technology can be used. Some examples of useful catalysts which can be employed are tertiary amines, such as tetramethyl-1,3-butane diamine, triethylene diamine, triethanolamine, N-methylmorpholine, N-ethylmorpholine, tribenzylamine, N,N-dimethylbenzylamine, as well as tin compounds, such as dibutyl tin dilaurate, stannous oleate, stannous octoate, and others.

Polyurethanes are used in both the unfoamed and the so-called foam form. The most preferred embodiment of the present invention is a flame retardant, self-extinguishing polyurethane foam comprising an organic polyol, sufficient organic polyisocyanate to combine with said polyol to produce polyurethane foam, a foam-forming catalyst, a blowing agent and a sufficient amount of tribromocumene to impart flame retardant properties to the polyurethane foam. Polyurethane foams may be either flexible or rigid. Polyurethane foams are normally prepared from diisocyanates and hydroxyl-terminated polyethers or polyesters. Linear or only slightly branched polymers are used to provide flexible foams, whereas more highly branched polymers produce rigid foams. Appropriate catalysts and stabilizers control the foam formation and cure. In general, a foamed polyurethane is produced when low boiling liquids or gaseous blowing agents, are incorporated into, or generated by, the polyurethane-foaming reactants. Blowing agents which may be employed in the preparation of foamed polyurethanes include, for example, water either alone or admixed with other compounds, such as an aqueous solution of the catalyst. When water is employed, it reacts with an excess of the isocyanate to generate carbon dioxide, thereby resulting in a foam. Water is well known as a blowing agent in the preparation of flexible polyurethane foam. Other useful blowing agents especially desirable in rigid polyurethane foams include the chlorinated and fluorinated alkanes having from one to about three carbon atoms, such as the chlorofluoromethanes, the chlorofluorethanes and the chlorofluorobutanes. The amount of blowing agents employed can be varied over a wide range as is well known to those skilled in the art depending primarily upon the density desired in the foam product.

A wetting agent or surface-active agent is generally necessary for production of high grade polyurethane foam since the foams may collapse or contain very large uneven cells. Numerous wetting agents have been found satisfactory. Non-ionic surfactants are preferred. Examples of common surface active agents include silicone compounds, silicone oil mixtures and the polyethylene glycol ethers of long chain alcohols. For most applications, the surfactant is employed in an amount equal to from about 1.5 to about 2.5 parts by weight per 100 parts by weight of the polyol blend in the foam-forming compositions. An emulsifier may also be used depending on the exact properties of the polyurethane desired.

In conducting the process, one employs a temperature which affords a reasonable rate of reaction and does not cause an untoward amount of undesirable side reactions. The exact reaction temperature employed is not critical. In general, one uses slightly elevated temperatures such as from about 40° C. to about 350° C. In general, the reaction is conducted under ambient pressures since these are most economical. However, the reaction pressure is not critical. Superatmospheric and subatmospheric pressures can be utilized if desired. In general, vacuum or partial vacuum offers no material advantage. Elevated pressures up to 1,000 psig or more can be utilized when it is desired to conduct the process at a temperature above the normal boiling point of one or more materials in the reaction mixture.

The reaction time is not critical, but depends to some extent on the inherent reactivity of the reactants and other reaction conditions employed. In general, reaction times of from about 15 minutes to ten days are sufficient.

Solvents are not necessary in the preparation of polyurethanes. However, suitable solvents include aromatic hydrocarbons such as benzene, xylene, toluene; the various chlorinated benzenes such as chlorobenzene; dimethoxylene glycol; dimethylformamide; or any other normally liquid material which is also liquid within the above-mentioned temperature range and non-reactive under the reaction conditions.

The flame-retarded urethane polymers of this invention can take the form of foamed products, elastomers, surface coatings and the like. They may be formed in accordance with any of the processing techniques known to the polyurethane art such as the prepolymer, quasi-prepolymer and "one-shot" techniques.

Tribromocumene may be prepared from cumene using bromine and a catalyst. Typical catalysts include $FeBr_3$, $SbCl_3$, $SnCl_4$, $AlCl_3$, $ZnCl_2$, $TiCl_4$ and metallic alumina. Approximately three equivalents of bromine are used per equivalent of cumene to produce tribrominated cumene.

The tribromocumene identified as an effective polyurethane flame retardant additive is actually represented by a group of isomers. The most frequently identified isomers observed in a tribromocumene mixture is 2,4,5-tribromocumene, 2,4,6-tribromocumene and 2,3,4-tribromocumene. 2,4,5-tribromocumene is generally present in the largest concentration.

In the preparation of tribromocumene a minor amount of impurities including dibromocumene and tetrabromocumene result. These impurities oftentimes possess flame retardant properties themselves.

The tribromocumene flame retardant of the present invention is not limited to polyurethanes and has application in a range of polymers. The two classes of polymers are the thermoset and the thermoplastic.

Thermoset polymers consist of the plastics which when subjected to heat, will normally become infusible or insoluble, and as such cannot be remelted. They have elaborately cross-linked three dimensional structures and are used for plastics, elastomers (lightly cross-linked), coatings and additives. The following are some of the commonly used compression-molded thermosetting compounds. They are obtained by condensation reactions between formaldehyde and substances such as melamine, phenol and urea. These compounds are melamine formaldehyde, phenol formaldehyde and urea formaldehyde. Another type of thermoset polymers include epoxies.

Incorporation of the flame retardant compounds of the present invention into a thermoset composition must be done before the polymer composition is complete. A variety of techniques to incorporate the flame retardant into the thermoset polymer are known in the art. The precursors of thermoset polymers are, generally, miscible powders or liquids. The flame retardant may be gradually blended into the precursors until it is distributed throughout the reaction mixture. The polymer composition is then cured and cross-linked.

In contrast to the thermoset polymers, most thermoplastic polymers can be made to soften and take a new shape by the application of heat and pressure. Thermoplastics consist of long-chain molecules often without any branching (e.g., high density polyethylene). Even if there is branching (e.g., low density polyethylene) the polymer may still be two dimensional. Thermoplastic polymers consist of those plastics which normally are rigid at operating temperatures, but can be remelted and reprocessed. They include polyethylene, polypropylene, polystyrene, polyvinyl chloride, acrylonitrile-butadiene-styrene (ABS), nylon, and the like.

Once the thermoplastic polymer is formed, the flame retardant compound of the present invention is incorporated into the polymer. Since thermoplastics soften or melt under heat and pressure, this enhances the dispersion of the flame retardant additive into the composition.

Tribromocumene is present polymer compositions including polyurethanes in an amount sufficient to impart flame retardant properties to the polymer. The tribromocumene is normally present in low concentrations. Frequently, it is present in a range of about 0.05-40 weight percent based on the weight of the entire polymer. Preferably, it is present in a range of about 1-20 weight percent based on the weight of the entire polymer.

Flame retardant compounds in addition to tribromocumene may be present in the polymer composition depending on the characteristics of the polymer desired. These additional flame retardant compounds may include other halogenated organic flame retardants or flame retardant phosphorus compounds well-known in the art.

Flame retardant synergists may also be employed in the preparation of the polymer compositions of the present invention. Inorganic synergists include antimony oxide, zinc oxide, zinc borate, and the like. Examples of organic synergists are tris-2-chloroethylphosphate, tris-2,3-dibromopropylphosphate, polyammonium phosphate, and the like.

The polymer composition can also have the usual fillers, dyes, pigments, plasticizers, anti-static agents, stabilizing agents, and the like incorporated therein, if desired.

The following examples illustrate the nature of the invention.

EXAMPLE 1

Preparation of TBC

To a nitrogen-dried 20-gal glass-lined reactor was charged 68.5 lbs (0.57 lb mole) cumene. After cooling to 4° C., 156 g (0.5 wt. % based on cumene) anhydrous $FeBr_3$ and 33 g (0.1 wt. %) nitromethane were added. Bromine (containing 12 ppm water) was fed into the liquid through a dipleg from a 10-gal drum. A glass wool plug was used in the bromine feed line to prevent solid contaminants from being introduced into the reactor. Pot temperature during the bromine addition was maintained at 2°-7° C. with glycol jacket cooling.

On the first day of the bromine addition, 213.4 lbs of bromine were added in 6 hrs. A nitrogen purge was placed on the system overnight and the empty bromine drum was replaced with a partial drum (containing 10 ppm water). On the second day, the reaction would not reinitiate with bromine (9.6 lbs added in 25 min) from the replacement drum. Even the addition of 42.7 g of fresh $FeBr_3$ did not promote the reaction. A fresh drum of bromine (10 ppm water) was then installed and an additional 43.2 lbs (266.2 lbs total, 1.666 lb mole) of bromine was added in 1 hr with the corresponding rapid evolution of HBr indicating the bromination was proceeding normally. The reaction mixture was warmed to 20° C. with water and then purged with nitrogen overnight to remove residual HBr.

The reaction mixture was washed in the 20-gal reactor with a saturated $Na_2SO_3$ solution (7.7 lbs $Na_2SO_3$ in 5 gal water) followed by a dilute $Na_2SO_3$ wash (1.1 lbs $Na_2SO_3$ in 5 gal water). The organic phase was filtered through a 100-micron fiberglass cartridge filter after the first wash and through a 1-micron filter after the second wash to give 185.7 lbs (96% yield) of cloudy yellow-brown crude TBC. A 12.4 sample of the crude product was dried with 140 g of anhydrous $MgSO_4$ and filtered to give 11.8 lbs of clear yellow TBC. Analysis of this crude product is given in Table 1.

The remaining 173.3 lbs of crude TBC was transferred to a 50-L flask for distillation through a 2-ft, 3-inch dimaeter, glass column containing about 1-ft of ceramic packing (Berl saddles). The cloudy appearance of the liquid was discharged by removing about 25 g of water with gentle heating under vacuum (about 5 torr). The product was then distilled over a four day period. After the third day of distillation the bottoms were transferred to a 12-L flask to ensure maximum distillate recovery. Analysis of this distilled product is given in Table 1. In addition to the fractions given in Table 1, about 80 g of water was recovered from the dry ice traps.

TABLE 1

|  | Crude Product | Distilled Product |
| --- | --- | --- |
| Appearance | Clear yellow liquid | Clear colorless liquid |
| GC Analysis |  |  |
| 2,4-dibromocumene | 0.2 (wt. %) | 0.1 (area %) |
| 2,4,5-tribromocumene | 88.6 | 93.3 |
| 2,4,6-tribromocumene* | 0.5 | 0.5 |
| 2,3,4-tribromocumene | 6.3 | 6.0 |
| tetrabromocumene | 3.5 | 0.1 |
| GC closure | 99.2 | 100.0 |

*Assumed structure

EXAMPLES 2-6

Examples 2-6 were prepared in a manner similar to Example 1. Examples 2-6 used varying amounts of $FeBr_3$ as a catalyst. The use of 0.1 wt % of nitromethane allowed only trace amounts of transalkylation impurities (dibromobenzene, tribromobenzene, dibromodiisopropylbenzene and tribromodiisopropylbenzene) to form.

Gas chromatographic analysis of the crude product was based on five categories. They are monobromocumene, ($C_9H_{11}Br$), dibromocumene ($C_9H_{10}Br_2$), tribromocumene ($C_9H_9Br_3$), tetrabromocumene ($C_9H_8Br_4$) and miscellaneous transalkylation impurities. Each component is given as weight percent of the entire product.

TABLE 2

| Example | wt. % $FeBr_3$ (based on cumene) | Crude Product Analysis (GC wt. %) | | | | Transalkyl Impurities | Crude Yield % | Distilled Yield % |
| --- | --- | --- | --- | --- | --- | --- | --- | --- |
|  |  | $C_9H_{11}Br$ | $C_9H_{10}Br_2$ | $C_9H_9Br_3$ | $C_9H_8Br_4$ |  |  |  |
| 2 | 0.6 | 0 | 0.1 | 98.4 | 1.5 | trace | 94 | 79 |
| 3 | 2.2 | 0 | 1.8 | 96.4 | 1.5 | 0.3 | 98 | 88 |
| 4 | 0.8 | 0 | 3.3 | 95.6 | 0.9 | trace | 90 | 78 |
| 5 | 0.8 | 0 | 3.0 | 95.7 | 1.0 | 0.3 | 93 | 93 |
| 6 | 0.8 | 0 | 0.3 | 96.7 | 2.6 | trace | 89 | 87 |

EXAMPLES 7-13

Performance Data

Table 4 contains information on a series of hand-mixed polyurethane foam containing varying amounts of tribromocumene. The composition of each foam is given in grams.

Poly G 71-530, a trademark of Olin Chemicals, is a sucrose-amine type polyether polyol with a hydroxyl number of 530±10.

PAPI 135, a trademark of Upjohn Polymer Chemicals, refers to a polymethylene polyphenylisocyanate with an average functionality of 2.7.

Dow Corning®193, a registered trademark of Dow Corning Corporation, is a monohydrolyzable silicone glycol copolymer surfactant designed for use in producing all types of rigid urethane foam.

Polycat 8, a trademark of Abbott Laboratories, refers to N,N'-dimethylcyclohexylamine, a tertiary amine catalyst.

T-12, a trademark of M and T Chemicals, refers to a dibutyl tin dilaurate catalyst containing 18% $Sn^{IV}$.

Freon 11B, available from E. I. duPont deNemours and Co., Inc., refers to trichlorofluoromethane, a blowing agent.

Phosgard®C-22-R, a registered trademark of Monsanto Industrial Chemicals Co., is a flame retardant organophosphorus polymer for use in a variety of polymer compositions including urethane foams.

Santicizer®141, a registered trademark of Monsanto Industrial Chemicals Co., is a general purpose plasticizer for commercial resins.

The sucrose-amine polyol, tribromocumene, surfactant, blowing agent, tin catalyst, amine catalyst and optionally the organophosphorus polymer or plasticizer were weighed and charged into a plastic container. The mixture was blended for 45 seconds with an electric mixer. The isocyanate component was then weighed and added to the mixture which was blended for 15 seconds. The mixture was then transferred to a cardboard box where the foam was allowed to rise. The entire procedure was carried out at room temperature.

Two tests were used to evaluate the flame retardant properties of these polyurethane foam compositions. They were the ASTM D-1692 and the Oxygen Index Test. ASTM D-1692 is a small-scale horizontal laboratory screening procedure for measuring the rate of burning or extent of burning the rigid or flexible cellular plastics such as polyurethane foams. The Oxygen Index Test is defined as the minimal volume fraction of oxygen in a slowly rising gaseous atmosphere that will sustain the candlelike burning of a stick of polymer. The higher the Oxygen Index of a molded article, the more flame retardant it is.

TABLE 3

| Example | 7 | 8 | 9 | 10 | 11 | 12 | 13 |
|---|---|---|---|---|---|---|---|
| Poly G 71-530 | 100 | 100 | 100 | 100 | 100 | 100 | 100 |
| PAPI 135 | | | | | | | |
| 110 Index | 139 | 139 | 139 | 139 | 139 | 139 | 139 |
| Dow Corning ® 193 | 1.5 | 1.5 | 1.5 | 1.5 | 1.5 | 1.5 | 1.5 |
| Polycat 8 | 2.5 | 2.5 | 2.5 | 1.0 | 2.5 | 2.5 | 2.5 |
| T-12 Catalyst | 0.03 | — | — | 0.1 | — | 0.03 | — |
| Freon 11 B | 38 | 40 | 40 | 43 | 40 | 42 | 40 |
| Tribromocumene | — | 10 | 20 | 30 | 20 | 20 | 30 |
| Phosgard C-22-R ® | — | — | — | — | 10 | — | — |
| Santicizer 141 ® | — | — | — | — | — | 5 | — |
| % Bromine | 0 | 2.7 | 5.1 | 7.4 | 4.9 | 5.0 | 7.4 |
| Density (lbs/ft$^3$) | 1.9 | 1.9 | 2.1 | 2.0 | 2.2 | 2.0 | 2.1 |
| Compression Strength | | | | | | | |
| Parallel (psi) | 39.1 | 27.2 | 28.2 | 40.8 | 33.9 | 40.0 | 28.3 |
| Perpendicular (psi) | 20.4 | 16.8 | 20.1 | 20.9 | 22.8 | 21.7 | 18.5 |
| Oxygen Index | 20.2 | 20.8 | 21.2 | 22.3 | 23.5 | 22.1 | 22.0 |
| ASTM D-1692 | | | | | | | |
| Burn Rate, (in/min) | 3.5 | 5.2 | 2.1 | 2.0 | 0.5 | 1.8 | 1.5 |
| Burn Extent (in) | 6.0 | 5.0 | 1.5 | 1.6 | 0.4 | 1.4 | 0.9 |
| Burn Time (sec) | 122 | 57.3 | 43.7 | 48.0 | 48.0 | 47.0 | 35.6 |

As indicated in Table 3, the polyurethane foam samples which contain tribromocumene have much higher ratings under the ASTM D-1692 burn test than the foam containing no tribromocumene.

I claim:
1. A flame retardant, self-extinguishing polyurethane foam comprising:
   (a) an organic polyol,
   (b) sufficient organic polyisocyanate to combine with said polyol to produce polyurethane foam,
   (c) a foam-forming catalyst,
   (d) a blowing agent and
   (e) a sufficient amount of tribromocumene to impart flame retardant properties to the polyurethane.
2. A polyurethane foam of claim 1 wherein said amount of tribromocumene is from about 0.05 to about 40 weight percent of the entire polyurethane foam.

* * * * *